United States Patent [19]

Strung

[11] Patent Number: 4,775,376
[45] Date of Patent: Oct. 4, 1988

[54] METHOD AND APPARATUS FOR CATCHING FLUIDS PURGED FROM A SYRINGE

[75] Inventor: Mark E. Strung, Dublin, Ohio

[73] Assignee: Erbamont, Inc., Dublin, Ohio

[21] Appl. No.: 883,892

[22] Filed: Jul. 9, 1986

[51] Int. Cl.⁴ ............................................. A61M 5/00
[52] U.S. Cl. .................... 604/415; 604/122; 604/198
[58] Field of Search .......... 604/49, 51, 56, 88, 604/110, 122, 125, 192, 197, 198, 200–202, 263, 408, 415; 128/764

[56] References Cited

U.S. PATENT DOCUMENTS

| | | | |
|---|---|---|---|
| 1,967,439 | 7/1934 | Heineman | 604/415 |
| 2,876,770 | 3/1959 | White | 604/198 |
| 3,073,306 | 1/1963 | Linder | 604/198 |
| 3,321,098 | 5/1967 | Ogle | 604/415 |
| 3,354,881 | 11/1967 | Bloch | 604/198 |
| 3,368,557 | 2/1968 | Hassing et al. | 128/221 |
| 4,044,758 | 8/1977 | Patel | 128/2 |
| 4,085,737 | 4/1978 | Bordow | 604/263 |
| 4,124,025 | 11/1978 | Alrazi | 128/218 |
| 4,328,802 | 5/1982 | Curley et al. | 604/88 |
| 4,362,158 | 12/1982 | Lena | 604/415 |
| 4,564,054 | 1/1986 | Gustavsson | 604/198 |
| 4,619,651 | 10/1986 | Kopfer et al. | 604/415 |
| 4,623,336 | 11/1986 | Pedicano et al. | 604/263 |
| 4,671,331 | 6/1987 | Pruden | 604/415 |

Primary Examiner—Dalton L. Truluck
Assistant Examiner—Frank Wilkens
Attorney, Agent, or Firm—Smith & Schnacke

[57] ABSTRACT

A syringe purging device comprises a closed chamber into which air and/or any excessive amount of a hazardous liquid, such as a chemotherapy drug, is ejected from a syringe to overcome the health hazard created by openly purging syringes into the air or into a pad of gauze material. A sharp open end of a hollow needle of a syringe is sealingly inserted into the chamber and the syringe is activated to purge any air and/or excess liquid into the chamber which expands as necessary. Preferably, the chamber is then further expanded to reduce the pressure therewithin to better ensure clean withdrawal of the needle from the chamber or extension of the needle beyond the chamber and retention within the chamber of any fluids ejected from the syringe.

2 Claims, 3 Drawing Sheets

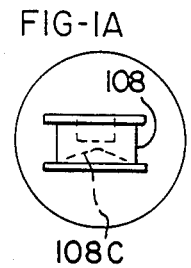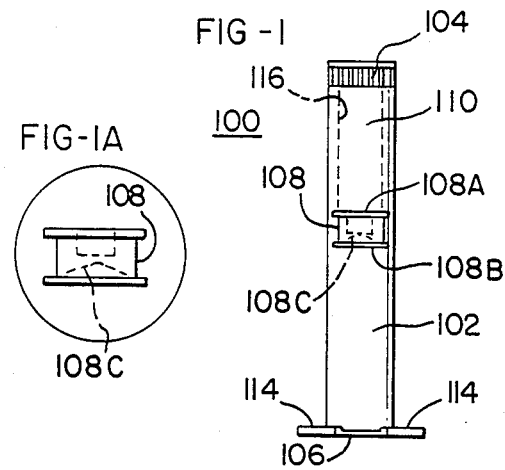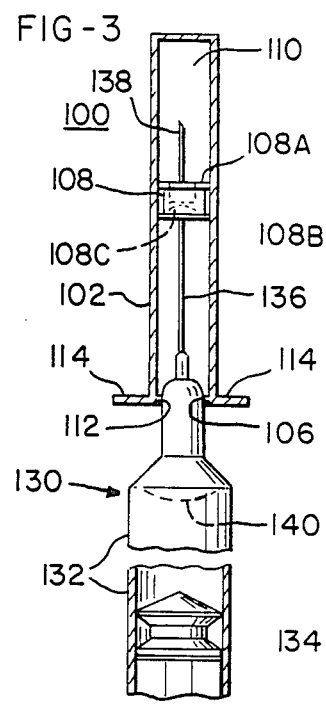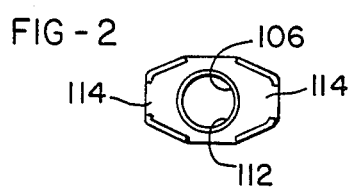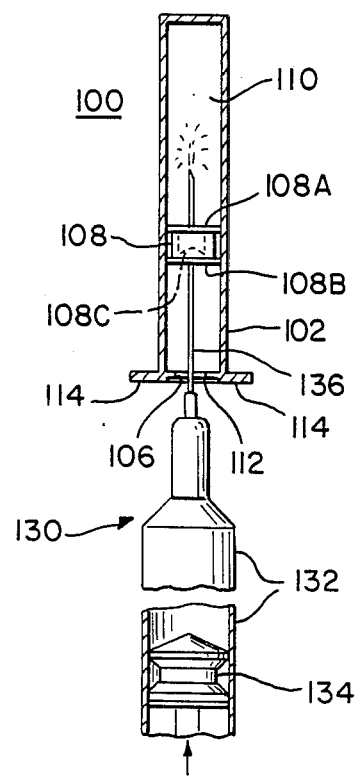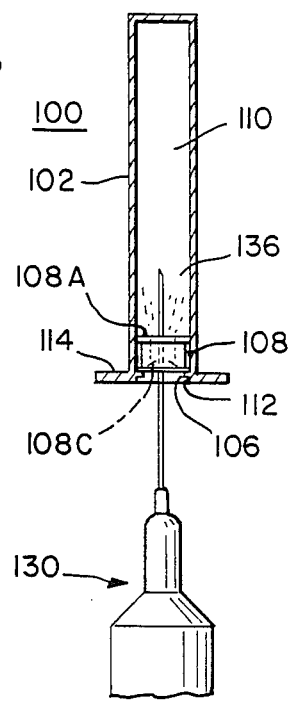

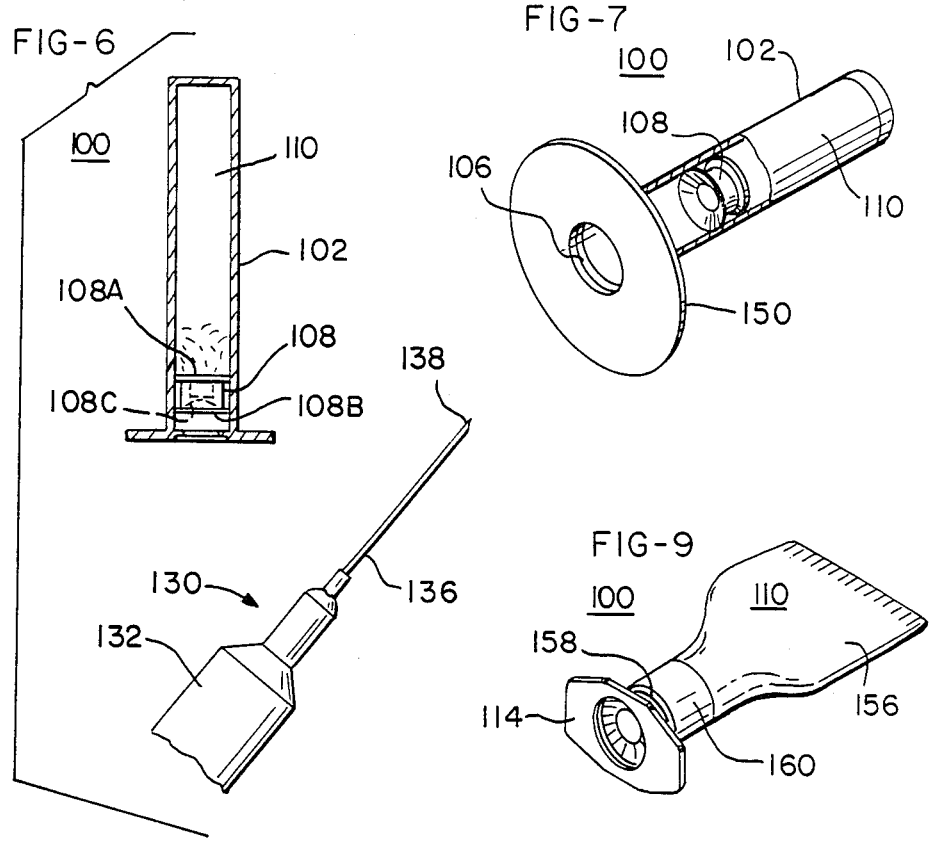

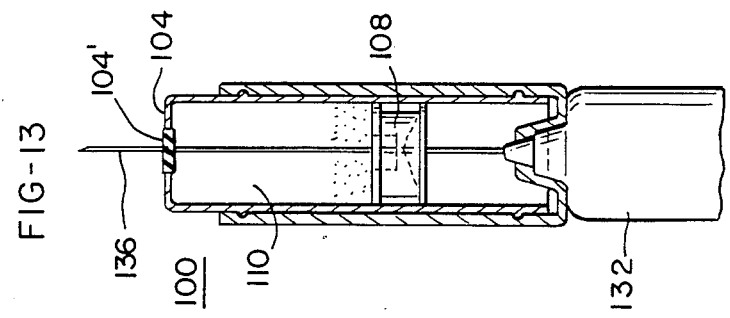
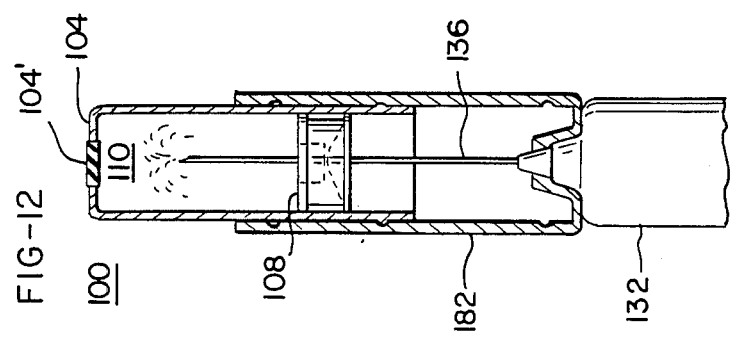
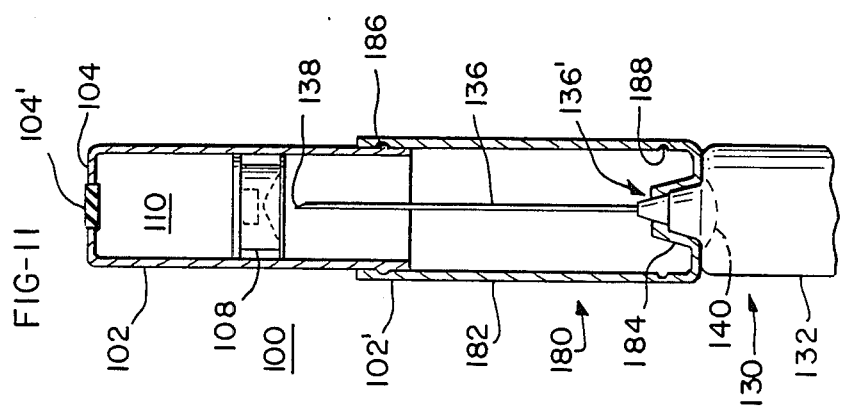

METHOD AND APPARATUS FOR CATCHING FLUIDS PURGED FROM A SYRINGE

BACKGROUND OF THE INVENTION

The present invention relates generally to syringes for the injection of medicines into the body, and more particularly, to a method and apparatus for catching fluids ejected from the needle of a syringe containing a hazardous or potentially hazardous liquid, such as a chemotherapy drug, as air and/or excess liquid is purged from the syringe.

The use of syringes for the hypodermic injection of medicines into the body through a hollow needle fixedly or detachedly forming a part of a syringe is commonplace in modern medicine. We have all anxiously witnessed the preparation of a syringe for a hypodermic injection. A nurse, doctor or other medical attendant draws an approximate dosage of a medicine into a barrel of the syringe from a vial by means of a plunger sealingly fitted within the barrel of the syringe. Almost invariably, air is included within the syringe barrel or the desired dosage exceeds that which is recommended. Accordingly, the syringe is held with the open end of its hollow needle extending generally upward and the plunger is inserted into the barrel to purge the air and/or excess medicine from the syringe prior to injection.

Usually, the purging spray from the needle is harmless and may be simply squirted into the air or into a pad of gauze material. However, some fluids held by a syringe for injection or otherwise are hazardous or potentially hazardous, for example chemotherapy drugs, and the conventional purging operation described creates a dangerous health hazard to personnel utilizing the syringe. It is, thus, apparent that the need exists for a method and apparatus for catching the spray which squirts from the open end of a hollow needle of a syringe when air and/or excessive portions of a hazardous or potentially hazardous liquid are purged from the syringe.

SUMMARY OF THE INVENTION

In accordance with the present invention, the health hazard created by openly purging air and/or an excessive amount of a hazardous liquid, in particular, a chemotherapy drug, from a syringe is overcome by catching the fluids purged from a syringe within a closed chamber.

According to one aspect of the present invention, a device for catching the fluids purged from a syringe comprises closed and expandable chamber means for receiving the sharp open end of a hollow needle of a syringe therewithin such that the syringe can be activated to purge any air and/or excess liquid from the syringe into the chamber and expand the chamber as necessary. Preferably, the chamber is further expanded, for example, by withdrawing the needle from the chamber which reduces the pressure therewithin to better ensure clean withdrawal of the needle and retention within the chamber of any fluids ejected from the syringe.

In a first embodiment of the syringe purging device of the present invention, the chamber comprises a tubular member having a closed end and an open end, with movable stopper means positioned within the tubular member. The stopper defines the fluid-receiving chamber of the device between it and the closed end of the tubular member. The stopper, while being movable within the tubular member, maintains an airtight seal with the tubular member and provides a sealed entryway into the chamber by the needle of a syringe puncturing the stopper. To ensure that the chamber is not opened by withdrawal of the stopper from the tubular member, restraint means are included adjacent the open end of the tubular member for abutting engagement with the stopper to prevent its removal as a needle is withdrawn from the stopper, and hence, from the chamber.

Flange means extend from the open end of the tubular member for facilitating handling and/or protecting the user of the syringe purging device. The tubular member of a syringe purging device in accordance with the present invention may also include a tapering, funnel-shaped entryway at its open end to facilitate insertion of a syringe needle into the device.

Compression of air contained within the chamber will generally maintain a minimum chamber size as a needle is inserted through the stopper. However, separate chamber maintaining means may be positioned within the chamber for limiting movement of the stopper toward the closed end of the tubular member to thereby ensure a minimum size for the chamber. Preferably, the tubular member of the syringe purging device of the present invention is formed from plastic and the stopper is formed from rubber, both of which are inert to liquids to be held by the device, for example, chemotherapy drugs.

In a second embodiment of the syringe purging device of the present invention, the chamber comprises an open ended first tubular member, with stopper means fixedly positioned within and closing one end thereof. The stopper means maintains an airtight seal of the closed end of the first tubular member and permits sealed entrance into the first tubular member by a needle of a syringe puncturing the stopper. A second tubular member is provided having a closed end and an open end. The open end of the second tubular member is sized to telescopically engage the open end of the first tubular member, and seal means are provided for airtight sealing of the telescopic engagement between the first and second tubular members. The first and second tubular members are intially in a collapsed state such that sidewalls of the first and secnd tubular members substantially overlap one another, with the chamber defined between the fixedly positioned stopper within the first tubular member and the closed end of the second tubular member.

A syringe may be purged using the second embodiment by inserting the open end of the hollow needle of a syringe into the chamber through the fixedly positioned stopper and activating the syringe to eject any air and/or excess liquid therefrom. The air and/or excess liquid from the syringe enters and expands the chamber as necessary by telescopically extending the second tubular member relative to the first tubular member. As the needle is withdrawn from the fixedly positioned stopper, and hence, the chamber, the air and/or excess liquid purged from the syringe is retained within the chamber. Alternately, the closed end of the second tubular member may include diaphragm means for permitting sealed extension of a needle of a syringe beyond the chamber by puncturing the diaphragm. If the device is operated in this manner, the syringe purging device remains on the needle while it is used for injection, typically into an intravenous tube or the like, and then is discarded with the syringe.

Preferably, the chamber may be further expanded by manually extending the second tubular member relative to the first tubular member to effect reduced pressure within the chamber prior to withdrawal or extension of the needle. It is noted that, where the closed end of the second tubular member includes a diaphragm, extension of the needle through the diaphragm will assist or perform the desired chamber expansion. Reduced pressure within the chamber better ensures clean withdrawal or extension of the needle and retention within the chamber of any fluids ejected from the syringe. Restraint means may be positioned adjacent the open ends of the second tubular member and/or the first tubular member to prevent the second tubular member from being disengaged from the first tubular member which would open the chamber.

In a third embodiment of the syringe purging device of the present invention, the chamber comprises collapsed bag-like means for receiving air and/or excess liquid ejected from a syringe, with the bag-like means being airtight and including a sealing member which permits sealed entrance into the chamber by a needle of a syringe puncturing the sealing member. Syringe purging devices of the present invention are made sterile, for example, by one of a variety of well known techniques used to sterilize plastic syringes, such that any liquid purged from a syringe can be redrawn into the syringe to arrive at a desired content. Syringe purging devices of the present invention can also conveniently be included in a needle cover, for example, for a prefilled syringe, to facilitate handling and use of hazardous liquids, and particularly, chemotheraphy drugs.

According to another aspect of the present invention, a method for catching fluids ejected from a sharp open end of a hollow needle of a syringe containing a chemotherapy drug as air and/or excess drug is purged from the syringe comprises the steps of: inserting the sharp open end of a hollow needle of a syringe into a closed chamber; manually operating the syringe to purge air and/or excess drug from the syringe into the chamber; and, withdrawing the needle from the chamber or extending the needle beyond the chamber.

According to yet another aspect of the present invention, a method for catching fluids ejected from a sharp open end of a hollow needle of a syringe containing a hazardous or potentially hazardous liquid as air and/or excess liquid is purged from the syringe comprises the steps of: inserting the sharp open end of a hollow needle of a syringe into a closed and expandable chamber; manually operating the syringe to purge air and/or excess liquid from the syringe, the air and/or excess liquid entering the chamber and expanding it as necessary; and, withdrawing the needle from the chamber or extending the needle beyond the chamber. The method according to this aspect of the present invention may further comprise the step of expanding the chamber to effect reduced pressure within the chamber after manually operating the syringe to purge it, the reduced pressure within the chamber better ensuring clean withdrawal or extension of the needle and retention within the chamber of any purged air and/or excess liquid.

It is, therefore, an object of the present invention to provide a method and apparatus for minimizing the health hazards associated with the use of a syringe containing hazardous or potentially hazardous liquids.

Another object of the present invention is to provide an improved method and apparatus for catching fluids which squirt from the needle of a syringe containing a hazardous or potentially hazardous liquid as air and/or excessive amounts of the liquid are purged from the syringe.

An additional object of the present invention is to provide a method and apparatus for catching fluids ejected from a sharp open end of a hollow needle of a syringe containing a chemotherapy drug as air and/or excess drug is purged from the syringe.

Other objects and advantages of the invention will be apparent from the following description, the accompanying drawings and the appended claims.

BRIEF DESCRIPTION OF THE DRAWINGS

FIG. 1 is a side view of a first embodiment of a syringe purging device in accordance with the present invention.

FIG. 2 is a bottom view of the syringe purging device of FIG. 1 showing the needle entrance opening of the device.

FIGS. 3–6 are partially sectioned side views of the syringe purging device of FIGS. 1 and 2 showing operation of the device for purging a syringe of air and/or excess liquid.

FIGS. 7–13 show alternate embodiments of syringe purging devices in accordance with the present invention.

DETAILED DESCRIPTION OF THE INVENTION

A number of embodiments of a syringe purging device in accordance with the present invention have been shown in the drawing figures wherein identical or corresponding parts have been identified by like reference numerals throughout. A first embodiment of a syringe purging device 100 in accordance with the present invention is shown in drawing FIGS. 1–6. The device 100 comprises a tubular member 102 having a closed end 104 and an open end 106. Movable stopper means, comprising a resilient stopper 108 in the first embodiment, is positioned within the tubular member 102 for defining closed and expandable chamber means. The closed and expandable chamber means comprises a chamber 110 which extends between the stopper 108 and the closed end 104 of the tubular member 102. While other materials can be used, preferably, the tubular member 102 is formed from translucent plastic and the stopper 108 is formed from rubber. The use of translucent plastic permits a clear view of the operation of the syringe purging device 100 to encourage proper and safe utilization. Whatever materials are used to construct a syringe purging device in accordance with the present invention, it should be understood that they must be inert to the liquids to be used by the syringe, for example, chemotherapy drugs for which the syringe purging device is particularly useful.

The stopper 108 comprises a generally cylindrical body having upper and lower sealing flanges 108A and 108B, respectively. The upper end of the stopper 108 is open and the lower end is closed by a concave lower wall 108C. The concave lower wall 108C of the stopper 108 is of an appropriate thickness such that it can be readily punctured by the sharp open end of a hollow needle of a syringe and provide sealing engagement with the needle to thereby maintain the chamber 110 closed yet in communication with the contents of a syringe via its hollow needle. The stopper 108 must also provide good resealability such that fluids contained within the chamber 110 will not leak and will be retained therein for an indefinite period of time after the syringe needle is withdrawn from the stopper 108.

Restraint means, comprising a raised rib 112 completely surrounding the open end 106 of the tubular member 102 in the first embodiment, abuttingly engages the stopper 108 as it is moved to the open end 106 of the tubular member 102 to prevent removal of the stopper 108 from the tubular member 102. The rib 112 thus prevents inadvertent opening of the chamber 110 during use of the syringe purging device 100. To facilitate handling and use of the device 100, flange means extend from the open end 106 of the tubular member 102. It is noted that the flange means can be of various shapes, for example, ranging from the diametrically opposed planar flanges 114 shown in drawing FIGS. 1–6 and 9 to an expanded circular flange 150 completely surrounding the open end 106 of the tubular member 102 as shown in FIG. 7. Expanded flanges, such as the circular flange 150, can also serve to shield and protect a user from accidental needle pricks as a syringe needle is inserted into the device 100.

Chamber maintaining means may be positioned within the chamber 110 for limiting movement of the stopper 108 toward the closed end 104 of the tubular member 102 to thereby define a minimum size for the chamber 110. The chamber maintaining means may take a variety of forms, for example, an auxiliary cylinder 116 as suggested in FIG. 1 or an inwardly projecting rib (not shown) extending partially or totally around the interior of the tubular member 102 comparable to the rib 112. Chamber maintaining means may not be needed in most syringe purging devices in accordance with the present invention since the air trapped within the chamber 110 will provide substantial resistance to movement of the stopper 108 toward the closed end 104 of the tubular member 102. However, chamber maintaining means may be desired to ensure that the stopper 108 is not advanced to the closed end 104 of the tubular member 102 due to off-center engagement of the stopper 108 by a syringe needle, which could possibly unseal the flanges 108A and 108B of the stopper 108, or to define a consistent minimum size for the chamber 110.

Reference is now made to FIGS. 3–6 which illustrate operation of a device in accordance with the present invention for purging a syringe of air and/or excess liquid. As shown in FIG. 3, a syringe 130 comprises a barrel 132 with a movable plunger 134 positioned therein for drawing fluids into the barrel 132 and ejecting fluids therefrom through a hollow needle 136 of the syringe 130. As is well known in the art, the sharp open end 138 of the needle 136 is inserted into a vial or dispensing container (not shown) which contains medicine to be injected by the syringe 130. The plunger 134 is inserted entirely into the barrel 132 and then withdrawn to draw medicine from the vial into the barrel 132 for a hypodermic injection.

Almost invariably air 140 will also be contained within the barrel 132 and/or the amount of medicine or other liquid desired to be drawn into the barrel 132 will exceed by a small amount the necessary quantity. In that event, the air and/or small amount of excess liquid contained within the barrel 132 must be purged prior to use of the syringe 130. As previously noted, usually the spray from the needle 136 is harmless and may be simply squirted into the air or into a pad of gauze material. However, some fluids held by the syringe 130 may be hazardous or potentially hazardous, such as a chemotherapy drug, such that performing the purging operation in the open air or into a pad of gauze material may be hazardous to personnel utilizing the syringe. In such cases, the syringe purging device 100 of the present invention is conveniently utilized as follows.

The sharp open end 138 of the needle 136 is inserted through the open end 106 of the tubular member 102 such that it engages the concave lower wall 108C of the stopper 108, preferably near its center, and is forced against the stopper 108 to puncture the lower wall 108C such that the open end 138 of the needle 136 is sealingly inserted into the closed and expandable chamber 110 of the device 100, as shown in FIG. 3.

The syringe 130 is then activated by forcing the plunger 134 into the barrel 132, with the needle 136 being in a generally upward direction such that air 140 within the barrel 132 is adjacent to and will be ejected through the needle 136 into the chamber 110 to purge the air 140 from the barrel 132. This purging operation is shown in FIG. 4 wherein the air 140 is ejected into the closed and expandable chamber 110. Some portion of the liquid contained within the barrel 132 is also ejected into the chamber 110, either inadvertently together with the air 140, or to eliminate excess liquid from the barrel 132 such that a desired quantity of the liquid is contained within the barrel 132. It is noted that syringe purging devices of the present invention are sterilized such that any liquid ejected from the syringe can be redrawn into the syringe if an excessive amount of the liquid is inadvertently ejected into the chamber 110.

As can be seen by reviewing FIGS. 3 and 4, the air 140 and/or excess liquid ejected from the syringe 130 into the chamber 110 expands the chamber 110 by moving the stopper 108 toward the open end 106 of the cylindrical member 102. Once the air 140 and any excess liquid has been purged from the barrel 132, the syringe needle 136 can be withdrawn from the stopper 108. Due to the tight sealing engagement of the lower concave wall 108C of the stopper 108, withdrawal of the needle 136 from the stopper 108 tends to move the stopper 108 toward the open end 106 of the tubular member 102 such that the stopper 108 may ultimately come into abutting engagement with the rib 112 surrounding the entrance to the open end 106 of the tubular member 102, as shown in FIG. 5.

Such movement of the stopper 108 further expands the chamber 110 and reduces the pressure therewithin to prevent any blow back problems, which may be encountered with vials, as the needle 136 is withdrawn from the device 100. The reduced pressure within the chamber 110 better ensures clean withdrawal of the needle 136 and retention within the chamber 110 of any fluids ejected from the syringe 130 such that the syringe 130 is ready to be used as shown in FIG. 6. The reduced pressure within the chamber 110 may lead to a slight withdrawal of the stopper 108 into the tubular member 102, as shown in FIG. 6; however, the sealing engagement of the stopper 108 with the interior of the tubular member 102 and the resealability characteristics of the stopper 108 ensure that the fluids ejected from the syringe 130 remain within the chamber 110.

Alternate embodiments of a syringe purging device in accordance with the present invention are shown in FIGS. 7–13. In FIG. 7, as previously described, the tubular member 102 of a syringe purging device 100 includes an expanded circular flange 150 completely surrounding the open end 106 of the tubular member 102 to provide a shield and protect a user from accidental needle pricks as a syringe needle is inserted into the device 100. As shown in FIG. 8, the open end 106 of the tubular member 102 of a syringe purging device 100 includes a tapering, funnel-shaped entryway 152 to facilitate insertion of a syringe needle into the device 100. In addition, flange means 154 can be provided at the inlet or wider end of the funnel-shaped entryway 152, with the flange means 154 ranging from the diametrically opposed planar flanges 114 as shown in FIGS. 1–6 and 9 to an expanded circular flange 150 as shown in FIG. 7.

As shown in FIG. 9, a syringe purging device 100 includes expandable chamber means which comprises collapsed bag-like means 156 for receiving air and/or excess liquid ejected from a syringe. The bag-like means 156 is airtight and includes a sealing member 158 which permits sealed entrance into the chamber or collapsed bag-like means 156 by a needle of a syringe puncturing the sealing member 158. As shown in FIG. 9, the sealing member 158 is a stopper fixedly positioned within a tubular member 160 which includes diametrically opposed planar flanges 114 comparable to those shown in FIGS. 1–6. In use, a needle of a syringe to be purged is inserted through the sealing member 158 of the syringe purging device 100 such that it extends into the chamber 110 defined by the end of the tubular member 160 which is closed by the collapsed bag-like means 156 sealingly extending therefrom. As any air and/or excess liquid is purged from the syringe, the collapsed bag-like means 156 expands as necessary to receive the air and/or excess liquid ejected from the syringe.

Another embodiment of a syringe purging device in accordance with the present invention is shown in FIG. 10. In this embodiment, the closed and expandable chamber means comprises an open ended first tubular member 164 having a sealing member 158 comprising a stopper fixedly positioned within and closing one of its ends while leaving the other end open. The sealing member 158 maintains an airtight seal of the closed end of the first tubular member 164 while permitting sealed entrance into the first tubular member 164 by a needle of a syringe puncturing the sealing member 158.

A second tubular member 166 has a closed end 168 and an open end 170. The opened end 170 of the second tubular member 166 is sized such that it can slidingly receive the first tubular member 164 to telescopically engage the open end of the first tubular member 164 and thereby form a chamber 110 defined between the sealing member 158 and the closed end of the second tubular member 166. It is noted that the second tubular member 166 could be sized to be received within the first tubular member 164 in accordance with this embodiment of the invention. Seal means taking the form of an O-ring 172 provide an airtight seal for the telescopic engagement between the first tubular member 164 and the second tubular member 166. Restraint means comprising an outwardly extending rib 174 on the upper open end of the first tubular member 164 provides for abutting engagement between the first tubular member 164 and the O-ring 172 or some portion of the second tubular member 166 to prevent inadvertent opening of the chamber 110 by disengagement of the first and second tubular members 164 and 166.

A syringe may be purged using the embodiment of FIG. 10 by inserting the open end of the hollow needle of a syringe into the chamber 110 through the sealing member 158 and activating the syringe to eject any air and/or excess liquid therefrom. The air and/or excess liquid from the syringe enters and expands the chamber 110 as necessary by telescopically extending the second tubular member 166 relative to the first tubular member 164, and is retained within the chamber as the needle is withdrawn from the sealing member 158, and hence, the chamber 110. Preferably, the chamber 110 may be further expanded by manually extending the second tubular member 166 relative to the first tubular member 164 to effect reduced pressure within the chamber 110 prior to withdrawal of the needle to thereby better ensure clean withdrawal of the needle and retention within the chamber 110 of any fluids ejected from the syringe.

Alternately, the closed end 168 of the second tubular member 166 may include diaphragm means 169 for permitting sealed extension of a needle of a syringe beyond the chamber 110 by puncturing the diaphragm 169. If the device 100 of FIG. 10 is used in this manner, the device 100 remains on the needle as it is used for injection, typically into an intravenous tube or the like, and then the device 100 is discarded with the syringe. It is apparent that the closed ends of the tubular members 102 of FIGS. 1–8 could also include diaphragms for extension of a needle beyond the corresponding chambers 110. However, extension of the needle in these embodiments is not preferred since it would tend to compress the chamber 110 rather than expand it. On the other hand, such use may be preferred in the embodiment of FIG. 10 since extension of a needle beyond the chamber 110 through the diaphragm 169 tends to expand the chamber 110, and hence, desirably reduce the pressure therein as previously noted. Finally, flange means 176, ranging from the diametrically opposed planar flanges 114 as shown in FIGS. 1–6 and 9 to the circular flange 150 as shown in FIG. 7 or another expanded flange, are provided adjacent to the end of the first tubular member 164 which is closed by the sealing member 158. It is noted that the sealing members 158 of the embodiments of FIGS. 9 and 10 could be diaphragms or the like which would close the devices as described yet permit sealed penetration of a syringe needle therethrough.

Yet another embodiment of a syringe purging device in accordance with the present invention is shown in FIGS. 11–13. In this embodiment, the device 100 is incorporated into a needle cover 180 used, for example, with a prefilled syringe 130. The needle cover 180 comprises a first tubular member 182 which includes an inwardly projecting base 184 which is sized to frictionally engage a base 136' of a needle 136 of a syringe 130. The syringe purging device 100 incorporated into the needle cover 180 comprises a second tubular member 102 which is slidingly engageable inside the first tubular member 182. The second tubular member 102 includes an outwardly extending rib 102' which is received within a first annular indentation 186 formed within the tubular member 182 to define a stable preuse configuration for the needle cover 180. A movable stopper 108 is positioned within the second tubular member 102 to define an expandable chamber 110 extending between the stopper 108 and the closed distal end 104 of the second tubular member 102. The closed distal end 104 of the second tubular member 102 in FIGS. 11–13 may include diaphragm means 104' as shown in the drawing figures.

When the syringe purging device 100 as illustrated in FIGS. 11–13 is used, for example, with a prefilled syringe 130, the syringe 130 and needle cover 80 come as a unit as shown in FIG. 11. A sharp end 38 of the syringe needle 136 is positioned just below the stopper 108 and outside the chamber 110. To purge air 140 or excess liquid contained within the syringe 130, the second tubular member 102 is telescopically collapsed into the first tubular member 182 such that the needle 136 penetrates the stopper 108 and extends into the chamber 110.

In this position, the plunger (not shown) of the syringe 130 is forced into the barrel 132 of the syringe 130 to expel the air 140 into the chamber 110 together with any liquid, such as chemotherapy drug, which may be contained within the syringe 130. As previously noted, the liquid injected into the chamber 110 may be inadvertently injected together with the air 140, or may comprise a small excessive amount of liquid prepackaged in the syringe 130. The syringe 130 together with the needle cover 180 are sterilized such that, if an excessive amount of the liquid contained within the syringe 130 is injected into the chamber 110, it can be redrawn into the syringe 130 such that the syringe 130 ultimately contains a sufficient amount of the liquid.

Once the syringe 130 is purged, as shown in FIG. 12, the needle may be withdrawn from the needle cover 180 and used for its intended purpose. Alternatively, the second tubular member 102 can be further telescopically collapsed into the first tubular member 182 such that the needle 136 extends beyond the chamber 110 by penetrating the diaphragm 104' as shown in FIG. 13. The syringe 130 can then be used, typically for injection of its contents into an intravenous tube or the like, and both the syringe 130 and the syringe purging device 100 still positioned on the needle 136 can be disposed of. It is noted that the second tubular member 102 could be returned to its original position if it is desirable to cover the needle 136 prior to disposal. Alternate positions of the second tubular member 102 within the first tubular member 182 can be defined by additional annular indentations, such as the indentation 188, formed within the first tubular member 182.

While the methods herein described and the forms of apparatus for carrying these methods into effect constitute preferred embodiments of this invention, it is to be understood that the invention is not limited to these precise methods and forms of apparatus, and that changes may be made in either without departing from the scope of the invention which is defined in the appended claims.

What is claimed is:

1. A syringe purging device comprising:

first tubular member having first and second opposing open ends;

stopper means fixedly positioned within and closing said first end, said stopper means being shaped to maintain an airtight seal of said first end and permit sealed entrance into said first tubular member by a needle of a syringe;

a second tubular member having a closed end and an open end and being sized such that said open end telescopically engages said second end of said first tubular member;

said closed end of said second tubular member including diaphragm means for permitting sealed extension of a syringe needle beyond said chamber by puncturing said diaphragm means, sufficiently to inject a patient; and means forming an airtight seal between said first and second tubular members.

2. A syringe purging device as claimed in claim 1 wherein said first and second tubular members include restraint means adjacent the open ends thereof for abutting engagement to prevent inadvertent opening of said chamber by disengaging said first and second tubular members.

* * * * *